(12) United States Patent
Kaddurah-Daouk

(10) Patent No.: US 6,169,115 B1
(45) Date of Patent: Jan. 2, 2001

(54) USE OF AMINOGUANIDINE ANALOGS FOR THE TREATMENT OF DISEASES OF THE NERVOUS SYSTEM

(76) Inventor: Rima Kaddurah-Daouk, 4 Ross Rd., Belmont, MA (US) 02178

( * ) Notice: Under 35 U.S.C. 154(b), the term of this patent shall be extended for 0 days.

(21) Appl. No.: 09/316,489

(22) Filed: May 21, 1999

Related U.S. Application Data

(60) Provisional application No. 60/086,504, filed on May 22, 1998, and provisional application No. 60/086,565, filed on May 22, 1998.

(51) Int. Cl.$^7$ .................................................. A61K 31/195
(52) U.S. Cl. .............................................................. 514/565
(58) Field of Search ............................................. 514/565

(56) References Cited

FOREIGN PATENT DOCUMENTS

WO 96/16031    5/1996    (WO) .

OTHER PUBLICATIONS

Brady, S. and Lasek, R., "Nerve–Specific Enolase and Creatine Phosphokinase in Axonal Transport: Soluble Proteins and the Axoplasmic Matrix," *Cell*, vol. 23, 515–23 (1981).

Burbaeva, GSh et al., "Decreased Level of Immunoreactive Phosphokinase BB Isoenzymes in the Brain of Patients with Schizophrenia and Senile Dementia of the Alzheimer Type," *Zh. Nevropatol. Psikhiatr Im S S Korsakova*, vol. 90, No. 7, 85–7 (1990)—abstract attached.

Cadoux–Hudson, T. et al., "Imaging of Human Brain Creatine Kinase Activity in Vivo," *FASEB J.*, vol. 3, 2660–6 (1989).

Chandler, W. et al., "Regional Creatine Kinase, Adenylate Kinase, and Lactate Dehydrogenase in Normal Canine Brain," *Stroke*, vol. 19, 251–5 (1988).

De Leon, M. et al., "Identification of Transcriptionally Regulated Genes After Sciatic Nerve Injury," *J. Neurosci. Res.*, vol. 29, 437–48 (1991).

Erecinska, M. and Silver, I., "ATP and Brain Function," *J. Cerebr. Blood Flow and Metabolism*, vol. 9, 2–19 (1989).

Friedhoff, A. and Lerner, M., "Creatine Kinase Isoenzyme Associated with Synaptosomal Membrane and Synaptic Vesicles," *Life Sci.*, vol. 20, 867–74 (1977).

Hemmer, W. and Wallimann, T., "Functional Aspects of Creatine Kinase in Brain," *Dev. Neuroscience*, vol. 15, 249–260 (1993).

Hemmer, W. et al., "Creatine Kinase Isoenzymes in Chicken Cerebellum: Specific Localization of Brain–type Creatine Kinase in Bergmann Glial Cells and Muscle–type Creatine Kinase in Purkinje Neurons," *Eur. J. Neuroscience*, vol. 6, 538–49 (1994).

Hertz, L. and Peng, L., "Energy Metabolism at the Cellular Level of the CNS," *Can. J. Physiol. Pharmacol.*, vol. 70, S145–57 (1992).

Ito, M., "The Cellular Basis of Cerebellar Plasticity," *Curr. Opin. Neurobiol.*, vol. 1, 616–20 (1991).

Khan, M.A., "Effect of Calcium on Creatine Kinase Activity of Cerebellum," *Histochem.*, vol. 48, 29–32 (1976).

Lim, L. et al., "Neurone–Specific Enolase and Creatine Phosphokinase are Protein Components of Rat Brain Synaptic Plasma Membranes," *J. Neurochem.*, vol. 41, 1177–82 (1983).

Maker, H.S. et al., "Regional Changes in Cerebellar Creatine Phosphate Metabolism During Late Maturation," *Exp. Neurol.*, vol. 38, 295–300 (1973).

Manos, P. et al., "Creatine Kinase Activity in Postnatal Rat Brain Development and in Cultured Neurons, Astrocytes, and Oligodendrocytes," *J. Neurochem.*, vol. 56, 2101–7 (1991).

Molloy, G. et al., "Rat Brain Creatine Kinase Messenger RNA Levels are High in Primary Cultures of Brain Astrocytes and Oligodendrocytes and Low in Neurons," *J. Neurochem.*, vol. 59, 1925–32 (1992).

Newman, E., "Regulation of Potassium Levels by Glial Cells in the Retina," *Trends in Neuroscience*, vol. 8, 156–9 (1985).

Oblinger, M. et al., "Cytotypic Differences in the Protein Composition of the Axonally Transported Cytoskeleton in Mammalian Neurons," *J. Neurol.*, vol. 7, No. 2, 453–62 (1987).

Orlovskaia, D.D. et al., "Neuromorphology and Neurochemistry of Senile Dementias in the Light of Studies on Glial Response," *Vestn Ross Akad Med Nauk.*, vol. 8, 34–9 (1992)—abstract only.

(List continued on next page.)

Primary Examiner—William R. A. Jarvis
(74) Attorney, Agent, or Firm—Lahive & Cockfield, LLP; Elizabeth A. Hanley, Esq.

(57) ABSTRACT

The present invention relates to the use of aminoguanidine compounds for treating diseases of the nervous system. Aminoguanidine compounds can be used as therapeutically effective agents against a variety of diseases of the nervous system such as diabetic and toxic neuropathies, peripheral nervous system diseases, Alzheimer's disease, Parkinson's disease, stroke, Huntington's disease, amyotropic lateral sclerosis, motor neuron disease, traumatic nerve injury, multiple sclerosis, dysmyelination and demyelination disorders, and mitochondrial diseases. The aminoguanidine compounds which can be used in the present method include (1) aminoguanidine and diaminoguanidine analogs which can act as substrates or substrate analogs for creatine kinase; (2) bisubstrate inhibitors of creatine kinase comprising covalently linked structural analogs of adenosine triphosphate (ATP) and aminoguanidine; (3) aminoguanidine analogs which can act as reversible or irreversible inhibitors of creatine kinase; and (4) N-phosphoroaminoguanidine analogs bearing nontransferable moieties which mimic the N-phosphoryl group.

13 Claims, No Drawings

OTHER PUBLICATIONS

Reichenbach, A., "Glial K+ Permeability and CNS K+ Clearance by Diffusion and Spatial Buffering," *Annals New York Acadamy of Science*, 272–86 (1991).

Roberts, J. and Walker, J., "Synthesis and Accumulation of an Extremely Stable High–Energy Phosphate Compound by Muscle, Heart, and Brain of Animals Fed the Creatine Analog, 1–Carboxyethyl–2–iminoimidazolidine (Homocyclocreatine)," *Arch. Biochem. Biophys.*, vol. 220, No. 2, 563–71 (1983).

Schiffman, R. et al. "Childhood Ataxia with Diffuse Central Nervous System Hypomyelination" *Ann. Neurol.*, vol. 35, No. 3, 331–340 (1994).

Stadhouders, A., et al., "Mitochondrial Creatine Kinase: A Major Constituent of Pathological Inclusions Seen in Mitochondrial Myopathies" *Proc. Natl. Acad. Sci.*, vol. 91(11), 5089–93 (1994).

USE OF AMINOGUANIDINE ANALOGS FOR THE TREATMENT OF DISEASES OF THE NERVOUS SYSTEM

RELATED APPLICATIONS

This application claims priority to U.S. Provisional Application Ser. No. 60/086,504 filed May 22, 1998, the entire contents of which are hereby incorporated herein by reference. The entire contents of each of PCT/US95/14567, filed Nov. 7, 1995, U.S. Ser. No. 08/336,388, filed Nov. 8, 1994, now abandoned, and U.S. Ser. No. 08/853,174, filed May 7, 1997 are hereby also incorporated herein by reference. The entire contents of each of U.S. Provisional Patent Application Ser. No. 60/086,565 filed on May 22, 1998 and U.S. patent application Ser. No. 09/316,918 entitled "Methods of Inhibiting Undesirable Cell Growth Using an Aminoguanidine Compound," filed on even date herewith, also are hereby expressly incorporated herein by reference.

BACKGROUND OF THE INVENTION

The nervous system is an unresting assembly of cells that continually receives information, analyzes and perceives it and makes decisions. The principle cells of the nervous system are neurons and neuroglial cells. Neurons are the basic communicating units of the nervous system and possess dendrites, axons and synapses required for this role. Neuroglial cells consist of astrocytes, oligodendrocytes, ependymal cells, and microglial cells. Collectively, they are involved in the shelter and maintenance of neurons. The functions of astrocytes are incompletely understood but probably include the provision of biochemical and physical support and aid in insulation of the receptive surfaces of neurons. In addition to their activities in normal brain, they also react to CNS injury by glial scar formation. The principle function of the oligodendrocytes is the production and maintenance of CNS myelin. They contribute segments of myelin sheath to multiple axons.

The ependyma cells react to injury mainly by cell loss. Microglial cells become activated and assume the shape of a macrophage in response to injury or destruction of the brain. These cells can also proliferate and adopt a rod-like form which could surround a tiny focus of necrosis or a dead neuron forming a glial nodule. Microglial degradation of dead neurons is called neuronophagia.

The creatine kinase/creatine phosphate energy system is only one component of an elaborate energy-generating system found in nervous system cells such as, for example, neurons, oligodendrocytes and astrocytes. The components of the creatine energy system include the enzyme creatine kinase, the substrates creatine and creatine phosphate, and the transporter of creatine. The reaction catalyzed by creatine kinase is: $MgADP_{\pm}PCr^{-}+H^{+}MgATP^{-}+Cr$. Some of the functions associated with this system include efficient regeneration of energy in cells with fluctuating and high energy demands, energy transport to different parts of the cell, phosphoryl transfer activity, ion transport regulation, and involvement in signal transduction pathways.

The creatine kinase/phosphocreatine system has been shown to be active in neurons, astrocytes, oligodendrocytes and Schwann cells. Manos et al., *J. Neurochem.* 56:2101–2107 (1991); Molloy et al., *J. Neurochem.* 59:1925–1932. The activity of the enzyme has been shown to be up-regulated during regeneration and down-regulated in degenerative states (see, e.g., *Annals Neurology* 35(3):331340 (1994); DeLeon et al., *J. Neurnosci. Res.* 29:437–448 (1991); Orlovskaia et al. *Vestnik Rossiiskoi Akademii Meditsinskikh Nauk.* 8:34–39 (1992). Burbaeva et al. *Shurnal Neuropathologll Psikhiatrii Imeni S-S-Korsakova* 90(7):85–87 (1990); Mitochondrial creatine kinase was recently found to be the major constituent of pathological inclusions seen in mitochondrial myopathies. Stadhouders et al., *PNAS,* 91, pp 5080–5093 (1994).

It is an object of the present invention to provide methods for treatment of diseases that affect cells of the nervous system that utilize the creatine kinase/phosphocreatine system using compounds which modulate the system.

SUMMARY OF THE INVENTION

The present invention pertains to methods of treating diseases of the nervous systems in an individual afflicted with such a disease by administering to the afflicted individual an amount of a compound or compounds which modulate one or more of the structural or functional components of the creatine kinase/phosphocreatine system sufficient to prevent, reduce or ameliorate the symptoms of the disease. Compounds which are effective for this purpose include aminoguanidines, e.g., aminoguanidine, diaminoguanidine, and analogs thereof.

The present invention also provides compositions containing aminoguanidino compounds, e.g., aminoguanidines or diaminoguandines, in combination with a pharmaceutically acceptable carrier, and effective amounts of other agents which act on the nervous system, to prophylactically and/or therapeutically treat a subject with a disease of the nervous system. The present invention further pertains to methods of use of aminoguanidino compounds in combination with other agents which act on the nervous system for treating diseases of the nervous system.

Packaged drugs for treating subjects having a disease of the nervous system or one who is predisposed to such diseases also are the subject of the present invention. The packaged drugs include a container holding the aminoguanidino compound, e.g., an aminoguanidine or diaminoguanidine, in combination with a pharmaceutically acceptable carrier, along with instructions for administering the same for the purpose of preventing, ameliorating, arresting or eliminating a disease of the nervous system.

Some of the diseases susceptible to treatment with aminoguanidino compounds, e.g., aminoguanidines or diaminoguanidines, according to the present invention include, but are not limited to Alzheimer disease, Parkinson's disease, Huntington's disease, motor neuron disease, diabetic and toxic neuropathies, traumatic nerve injury, multiple sclerosis, acute disseminated encephalomyelitis, acute necrotizing hemorrhagic leukoencephalitis, diseases of dysmyelination, mitochondrial diseases, fungal and bacterial infections, migrainous disorders, stroke, aging, dementia, and mental disorders such as depression and schizophrenia.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The methods of the present invention generally comprise administering to an individual afflicted with a disease of the nervous system an amount of a compound or compounds which modulate one or more of the structural or functional components of the creatine kinase/phosphocreatine system sufficient to prevent, reduce or ameliorate symptoms of the disease. Components of the system which can be modulated include the enzyme creatine kinase, the substrates creatine and creatine phosphate, and the transporter of creatine. As used herein, the term "modulate" means to change, affect or interfere with the normal functioning of the component in the creatine kinase/phosphocreatine enzyme system.

Compounds which are particularly effective for this purpose include aminoguanidine, aminoguanidines, diaminoguanidine, diaminoguanidines and analogs thereof which are described in detail below. The term "aminoguanidine compounds" will be used herein to include aminoguanidines and diaminoguanidines, such as aminoguanidine phosphate, and compounds which are structurally similar to aminoguanidine or aminoguanidine phosphate, and analogs of aminoguanidine and aminoguanidine phosphate. The term "aminoguanidine compounds" also includes compounds which "mimic" the activity of aminoguanidine and diaminoguanidine, such as aminoguanidine, aminoguanidine phosphate or aminoguanidine analogs, i.e., compounds which inhibit or modulate the creatine kinase system. The term "aminoguanidine" is intended to not include guanidine. The term "mimics" is intended to include compounds which may not be structurally similar to aminoguanidine or diaminoguanidine but mimic the therapeutic activity of these compounds, such as aminoguanidine, aminoguanidine phosphate or structurally similar compounds. The term "inhibitors of creatine kinase system" are compounds which inhibit the activity of the creatine kinase enzyme, molecules that inhibit the creatine transporter or molecules that inhibit the binding of the enzyme to other structural proteins or enzymes or lipids. The term "modulators of the creatine kinase system" are compounds which modulate the activity of the enzyme, or the activity of the transporter of creatine or the ability of other proteins or enzymes or lipids to interact with the system. The term "aminoguanidine analog" is intended to include compounds which are structurally similar to aminoguanidine or diaminoguanidine compounds such as aminoguanidine phosphate compounds which are art-recognized as being analogs of aminoguanidine or aminoguanidine phosphate, and/or compounds which share the same or similar function as aminoguanidine or aminoguanidine phosphate.

The language "treating diseases of the nervous system" is intended to include prevention of the disease, amelioration and/or arrest of a preexisting disease, and the elimination of a preexisting disease. The aminoguanidine analogs, e.g., aminoguanidine and/or diaminoguanidine compounds, described herein have both curative and prophylactic effects on disease development and progression.

The language "therapeutically effective amount" is intended to include the amount of the aminoguanidine compound sufficient to prevent onset of diseases of the nervous system or significantly reduce progression of such diseases in the subject being treated. A therapeutically effective amount can be determined on an individual basis and will be based, at least in part, on consideration of the severity of the symptoms to be treated and the activity of the specific analog selected if an analog is being used. Further, the effective amounts of the aminoguanidine compound may vary according to the age, sex and weight of the subject being treated. Thus, a therapeutically effective amount of the aminoguanidine compound can be determined by one of ordinary skill in the art employing such factors as described above using no more than routine experimentation in clinical management.

The language "pharmaceutically acceptable carrier" is intended to include substances capable of being coadministered with the aminoguanidine compound and which allows the active ingredient to perform its intended function of preventing, ameliorating, arresting, or eliminating a disease (s) of the nervous system. Examples of such carriers include solvents, dispersion media, adjuvants, delay agents and the like. The use of such media and agents for pharmaceutically active substances is well known in the art. Any conventional media and agent compatible with the aminoguandine compound may be used within this invention.

The term "pharmaceutically acceptable salt" is intended to include art recognized pharmaceutically acceptable salts. Typically these salts are capable of being hydrolyzed under physiological conditions. Examples of such salts include sodium, potassium and hemisulfate. The term further is intended to include lower hydrocarbon groups capable of being hydrolyzed under physiological conditions, i.e. groups which esterify the carboxyl moiety, e.g. methyl, ethyl and propyl.

The term "subject" is intended to include living organisms susceptible to having diseases of the nervous system, e.g. mammals. Examples of subjects include humans, dogs, cats, horses, cows, goats, rats and mice. The term "subject" further is intended to include transgenic species.

The language "diseases of the nervous system" is intended to include diseases of the nervous system whose onset, amelioration, arrest, or elimination is effectuated by the aminoguanidine compounds described herein. Examples of types of diseases of the nervous system include demyelinating, dysmyelinating and degenerative diseases Examples of locations on or within the subject where the diseases may originate and/or reside include both central and peripheral loci. As the term "disease" is used herein, it is understood to exclude, and only encompass maladies distinct from, neoplastic pathologies and tumors of the nervous system, ischemic injury and viral infections of the nervous system. Examples of types of diseases suitable for treatment with the methods and compounds of the instant invention are discussed in detail below.

Diseases of the Nervous System

Diseases of the nervous system fall into two general categories: (a) pathologic processes such as infections, trauma and neoplasma found in both the nervous system and other organs; and, (b) diseases unique to the nervous system which include diseases of myelin and systemic degeneration of neurons.

Of particular concern to neurologists and other nervous system practitioners are diseases of: (a) demyelination which can develop due to infection, autoimmune antibodies, and macrophage destruction; and, (b) dysmyelination which result from structural defects in myelin.

Diseases of neurons can be the result of: (a) aberrant migration of neurons during embryogenesis and early stage formation; or (b) degenerative diseases resulting from a decrease in neuronal survival, such as occurs in, for example, Alzheimer's disease, Parkinson's disease, Huntington's disease, motor neuron disease, ischemia-related disease and stroke, and diabetic neuropathy.

Demyelinating Diseases:

Primary demyelination is a loss of myelin sheaths with relative preservation of the demyelinated axons. It results either from damage to the oligodendroglia which make the myelin or from a direct, usually immunologic or toxic attack on the myclin itself. Secondary demyelination, in contrast, occurs following axonal degeneration. The demyelinating diseases are a group of CNS conditions characterized by extensive primary demyelination. They include multiple sclerosis and its variants and perivenous encephalitis. There are several other diseases in which the principal pathologic change is primary demyelination, but which are usually conveniently classified in other categories such as inborn errors of metabolism, the leukodystrophies, viral disease (progressive multifocal leukoencephalopathy PM), as well as several other rare disorders of unclear etiology.

Multiple Sclerosis (MS)

Multiple sclerosis is a disease of the central nervous system (CNS) that has a peak onset of 30–40 years. It affects all parts of the CNS and causes disability related to visual, sensory, motor, and cerebellar systems. The disease manifestations can be mild and intermittent or progressive and devastating.

The pathogenesis is due to an autoimmune attack on CNS myelin. The treatments available are symptomatic treating spasticity, fatigue, bladder dysfunction, and spasms. Other treatments are directed towards stopping the immunologic attack on myelin. These consist of corticosteroids such as prednisone and methylprednisolone, general immunosuppressants such as cyclophosphamide and azathioprine, and immunomodulating agents such as beta-interferon. No treatments are available to preserve myelin or make it resistant to attacks.

Acute Disseminated Encephalomyelitis

Acute Disseminated Encephalomyelitis usually occurs following a viral infection and is thought to be due to an autoimmune reaction against CNS myelin, resulting in paralysis, lethargy, and coma. It differs from MS by being a monophasic disease whereas MS is characterized by recurrence and chronicity. Treatment consists of administration of steroids.

Acute Necrotizing Hemorrhagic Leukoencephalitis

This is a rare disease that is generally fatal. It is also thought to be mediated by autoimmune attack on CNS myelin that is triggered by a viral infection. Neurologic symptoms develop abruptly with headache, paralysis and coma. Death usually follows within several days. Treatment is supportive.

Leukodystrophies:

These are diseases of the white matter resulting from an error in the myelin metabolism that leads to impaired myelin formation. They are thought of as dysmyelinating diseases, and can become manifest at an early age.

Metachromatic Leukodystrophy: an autosomal recessive (inherited) disorder due to deficiency of the enzyme arylsulfatase A leading to accumulation of lipids. There is demyelination in the CNS and peripheral nervous system leading to progressive weakness and spasticity.

Krabbe's disease: Also inherited as autosomal recessive and due to deficiency 15 of another enzyme: galctocerebroside beta-galactosidase.

Adrenoleukodystrophy and adrenomyeloneuropathy: affect the adrenal glad in addition to the nervous system.

No treatment is available to any of the leukodystrophies except for supportive treatment.

Degenerative Diseases:

There is no good etiology or pathophysiology known for these diseases, and no compelling reason to assume that they all have a similar etiology. Diseases under this category have general similarities. They are diseases of neurons that tend to result in selective impairment, affecting one or more functional systems of neurons while leaving others intact.

Parkinson's Disease:

Parkinson's disease is due to loss of dopaminergic neurons in the substantia nigra of the brain. It is manifested by slowed voluntary movements, rigidity, expressionless face and stooped posture. Several drugs are available to increase dopaminergic function such as levodopa, carbidopa, bromocriptine, pergolide, or decrease cholinergic function such as benztropine, and amantadine. Selegiline is a new treatment designed to protect the remaining dopaminergic neurons.

Spinocerebellar Degenerations

This is a group of degenerative diseases that affects in varying degrees the basal ganglia, brain stem, cerebellum, spinal cord, and peripheral nerves. Patients present symptoms of Parkinsonism, ataxia, spasticity, and motor and sensory deficits reflecting damage to different anatomic areas and/or neuronal systems in the CNS.

Degenerative Disease Affecting Motor Neurons

Included in this category are diseases such as amyotrophic lateral sclerosis (ALS), and spinal muscular atrophy. They are characterized by degeneration of motor neurons in the CNS leading to progressive weakness, muscle atrophy, and death caused by respiratory failure. Treatments are only symptomatic, there are no available treatments to slow down or stop the disease.

Alzheimer Disease (AD):

This disease is characterized clinically by slow erosion of mental function, culminating in profound dementia. The diagnostic pathologic hallmark of AD is the presence of large numbers of senile plagues and neurofibrillary tangles in the brain especially in neocortex and hippocampus. Loss of specific neuron populations in these brain regions and in several subcortical nuclei correlates with depletion in certain neurotransmitters including acetylcholine. The etiology of AD is still unknown. To date a lot of research has focused on the composition and genesis of the B/A4 amyloid component of senile plagues. Alzheimer's disease is characterized clinically by the slow erosion of intellectual function with the development of profound dementia. There are no treatments that slow the progression.

Huntington Disease (HD):

HD is an autosomal dominant disorder of midlife onset, characterized clinically by movement disorder, personality changes, and dementia often leading to death in 15–20 years. The neuropathologic changes in the brain are centered in the basal ganglia. Loss of a class of projection neurons, called "spiny cells" because of their prominent dendritic spinous processes, is typical. This class of cells contains gamma-aminobutyric acid (GABA), substance P, and opioid peptides. Linkage studies have localized the gene for HD to the most distal band of the short arm of chromosome 4. No treatments are available that have been shown to retard progression of the disease. Experimental studies showing a similarity between neurons that are susceptible to N-methyl d-aspartate (NMDA) agonists and those that disappear in HD has led to encouraging speculation that NMDA antagonists might prove beneficial. Some recent studies suggest that a defect in brain energy metabolism might occur in ~D and enhance neuronal vulnerability to excitotoxic stress.

Mitochondrial Encephalomyopathies:

Mitochondrial encephalomyopathies are a heterogenous group of disorders affecting mitochondrial metabolism. These deficits could involve substrate transport, substrate utilization, defects of the Krebs Cycle, defects of the respiratory chain, and defects of oxidation/phosphorylation coupling. Pure myopathies vary considerably with respect to age at onset, course (rapidly progressive, static, or even reversible), and distribution of weakness (generalized with respiratory failure, proximal more than distal facioscapulohumeral, orbicularis and extraocular muscles with ptosis and progressive external ophthalmoplegia). Patients with mitochondrial myopathies complain of exercise intolerance and premature fatigue.

Peripheral Nervous System Disorders

The peripheral nervous system (PNS) consists of the motor and sensory components of the cranial and spinal nerves, the autonomic nervous system with its sympathetic and parasympathetic divisions, and the peripheral ganglia. It is the conduit for sensory information to the CNS and effector signals to the peripheral organs such as muscle. Contrary to the brain, which has no ability to regenerate, the pathologic reactions of the PNS include both degeneration and regeneration. There are three basic pathological processes: Wallerian degeneration, axonal degeneration and segmental demyelination that could take place.

Some of the neuropathic syndromes include:

Acute ascending motor paralysis with variable sensory disturbance; examples being acute demyelinating neuropathics, infectious mononucleosis with polyneuritis, hepatitis and polyneuritis, toxic polyneuropathies.

Subacute sensorimotor polyneuropathy; examples of acquired axonal neurophathics include paraproteinemias, uremia diabetes, amyloidosis, connective tissue diseases and leprosy. Examples of inherited diseases include mostly chronic demyelination with hypertrophic changes, such as peroneal muscular atrophy, hypertrophic polyneuropathy and Refsum's diseases.

Chronic relapsing polyneuropathy; such as idiopathic polyneuritis porphyria, Beriberi and intoxications.

Mono or multiple neuropathy; such as pressure palsies, traumatic palsies, serum neuritis, zoster and leprosy.

Aminoguanidine Compounds Useful for Treating Nervous System Diseases

Aminoguanidine compounds useful in the present invention include compounds which modulate one or more of the structural or functional components of the creatine kinase/phosphoaminoguanidine system. Compounds which are effective for this purpose include aminoguanidine, aminoguanidine phosphate and analogs thereof, compounds which mimic their activity, and salts of these compounds as defined above. Exemplary aminoguanidine compounds are described below.

Aminoguanidine analogs and other agents which act to interfere with the activity of creatine biosynthetic enzymes or with the creatine transporter are useful in the present method of treating nervous system diseases. In the nervous system, there are many possible intracellular, as well as extracellular, sites for the action of compounds that inhibit, increase, or otherwise modify, energy generation through brain creatine kinase and/or other enzymes which are associated with it. Thus the effects of such compounds can be direct or indirect, operating by mechanisms including, but not limited to, influencing the uptake or biosynthesis of creatine, the function of the creatine phosphate shuttle, inhibiting the enzyme activity, or the activity of associated enzymes, or altering the levels of substrates or products of a reaction to alter the velocity of the reaction.

Substances known or believed to modify energy production through the creatine kinase/phosphocreatine system which can be used in the present method are described below. Exemplary compounds are shown in Table 1.

TABLE 1

Aminoguanidine Analogs

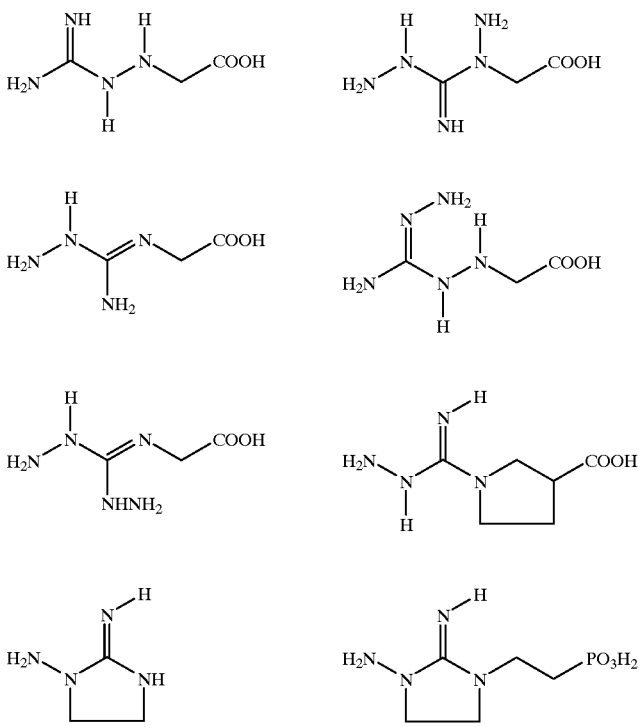

TABLE 1-continued

Aminoguanidine Analogs

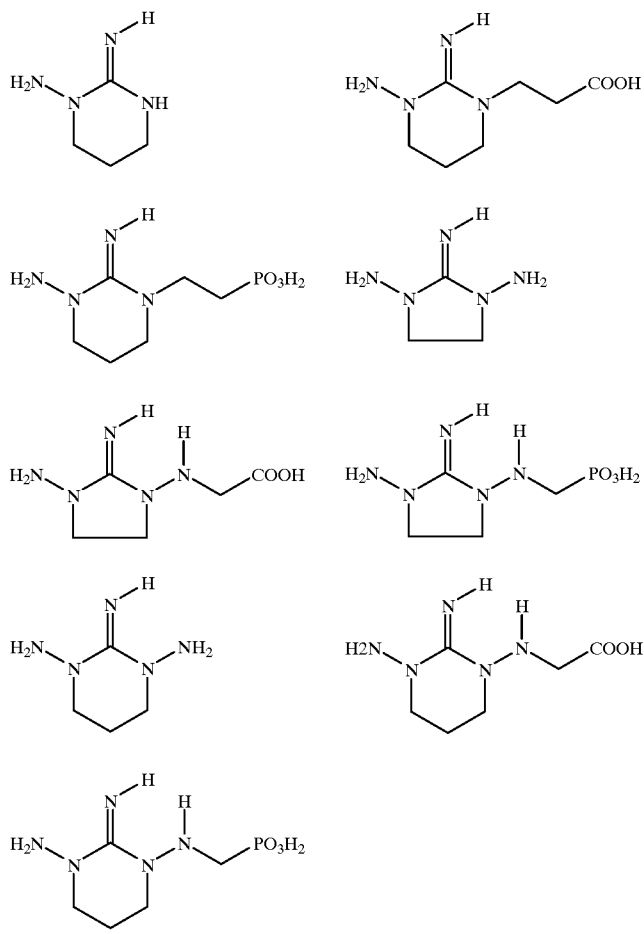

It will be possible to modify the substances described below to produce analogs which have enhanced characteristics, such as greater specificity for the enzyme, enhanced stability, enhanced uptake into cells, or better binding activity.

Compounds which modify the structure or function of the creatine kinase/creatine phosphate system directly or indirectly are useful in preventing and/or treating diseases of the nervous system characterized by up regulation or down regulation of the enzyme system.

In diseases where the creatine kinase/creatine phosphate system is down regulated, for example, uncontrolled firing of neurons, molecules useful for treating these diseases include those that will up regulate the activity, or could support energy (ATP) production for a longer period of time.

In diseases where the creatine kinase/creatine phosphate system is up regulated, the molecules that are useful include those that will down regulate the activity and/or inhibit energy production (ATP).

Molecules that regulate the transporter of creatine, or the association of creatine kinase with other protein or lipid molecules in the membrane, the substrates concentration creatine and creatine phosphate also are useful in preventing and/or treating diseases of the nervous system.

Compounds which are useful in the present invention can be inhibitors, substrates or substrate analogs, of creatine kinase, which when present, could modify energy generation or high energy phosphoryl transfer through the creatine kinase/phosphocreatine system. In addition, modulators of the enzymes that work in conjunction with creatine kinase now can be designed and used, individually, in combination or in addition to other drugs, to make control of the effect on brain creatine kinase tighter.

The pathways of biosynthesis and metabolism of creatine and creatine phosphate can be targeted in selecting and designing compounds which may modify energy production or high energy phosphoryl transfer through the creatine kinase system. Compounds targeted to specific steps may rely on structural analogies with either creatine or its precursors. Novel aminoguanidine analogs differing from aminoguanidine by substitution, chain extension, and/or cyclization may be designed. The substrates of multisubstrate enzymes may be covalently linked, or analogs which mimic portions of the different substrates may be designed. Nonhydrolyzable phosphorylated analogs can also be designed to mimic creatine phosphate without sustaining ATP production.

A number of aminoguanidine and aminoguanidine phosphate analogs have been previously described in the literature or can be readily synthesized. Examples are these shown in Table 1. Some of them are slow substrates for creatine kinase.

Some currently preferred aminoguanidine compounds of this invention are those encompassed by the general formula I

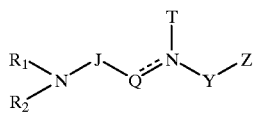

wherein
a) $R_1$ through $R_{16}$, if present, are selected from the group consisting of hydrogen, alkyl, alkenyl, alkynyl, and alkoxyl;
b) J is either

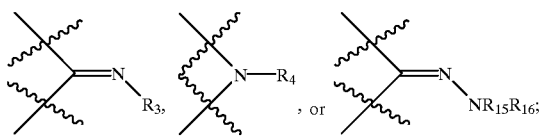

c) Q is either

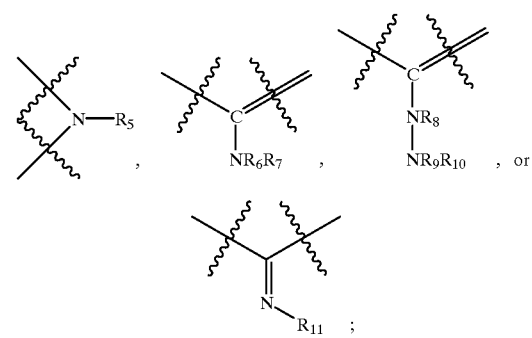

d) T, if present, is $R_{12}$ or $NR_{13}R_{14}$;
e) Y is an alkylene, alkenylene, alkynylene or an alkoxylene;
f) Z is selected from the group consisting of

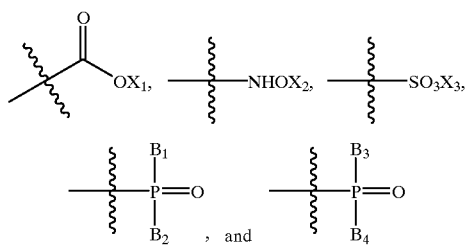

wherein $B_1$–$B_4$ are each independently selected from hydrogen and $OX_4$ and $X_1$–$X_4$ are each independently selected from the group consisting of hydrogen, alkyl, alkenyl, alkynyl and pharmaceutically acceptable salts; and
wherein Y and Q or N and Q can form a ring structure.

The alkylene, alkenylene, alkynylene, alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkoxy, haloalkyl, alkoxyene, and haloalkylene groups (hereinafter substituted hydrocarbon groups) are alkyl or alkylene groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups.

The language "pharmaceutically acceptable salt" (as a possibility for "X" in formula (I) and as it pertains to aminoguanidine compound salts) is intended to include pharmaceutically acceptable salts capable of being solvated under physiological conditions. Examples of such salts include sodium, e.g. disodium, potassium, e.g. dipotassium, and hemisulfate. The term is further intended to include lower hydrocarbon groups capable of being solvated under physiological conditions, i.e. alkyl esters, e.g. methyl, ethyl and propyl esters.

The nitrogen of formula I and Q or Q and Y can form a ring. The ring can be a hydrocarbon ring or a hetero ring containing atoms such as O, N or S. The ring structure further can be a single ring or alternatively can be a fused ring system. The preferred ring structures are single rings having five, six or seven ring members and most preferably five membered rings such as those present in cycloaminoguanidine- or carboaminoguanidine-like compounds, e.g.,

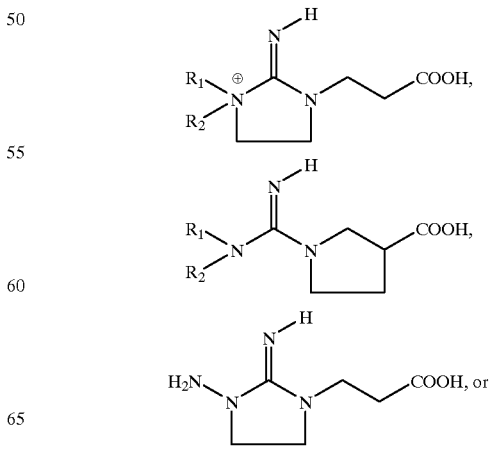

-continued

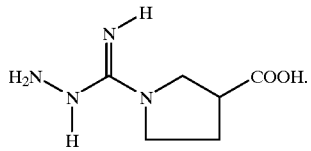

In one aspect of the invention, aminoguanidine compounds include

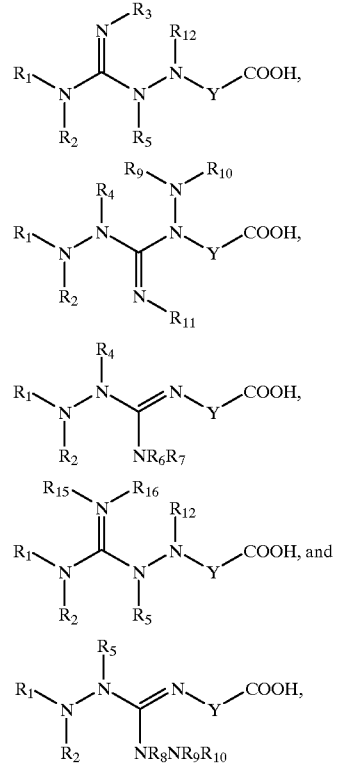

wherein $R_1$–$R_{16}$ and Y are as defined above. Optionally $R_2$ and $R_5$ or $R_2$ and $R_6$ or $R_2$ and $R_8$, together, can form a ring.

In another aspect of the invention, aminoguanidine compounds include

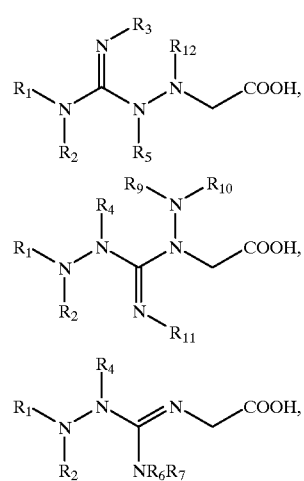

-continued

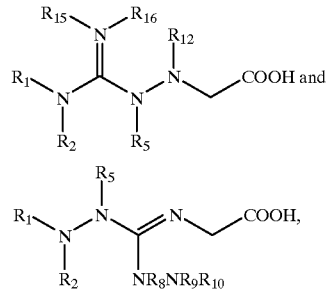

wherein $R_1$–$R_{16}$ are as described above. Optionally $R_2$ and $R_5$ or $R_2$ and $R_6$ or $R_2$ and $R_8$, together, can form a ring.

Preferred aminoguanidine compounds of the invention are

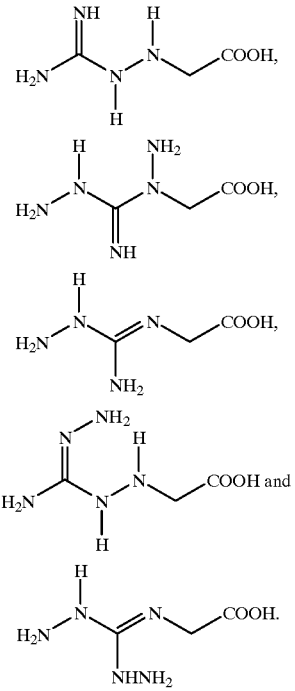

Aminoguanidine, aminoguanidine phosphate and many aminoguanidine analogs, and competitive inhibitors are commercially available and/or have been previously synthesized and are known in the literature.

Synthesis of guanidinoalkylcarboxylic acids can be accomplished by condensation of substituted or unsubstituted amino acid with a substituted or unsubstituted cyanamide. For example, 3-guanidinopropionic acid is commercially available and can be prepared as follows:

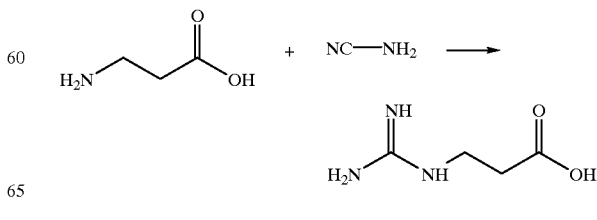

Preparation of [1-(hydrazinoiminomethyl)hydrazino]-acetic acids of the invention can be accomplished by the following synthetic procedure:

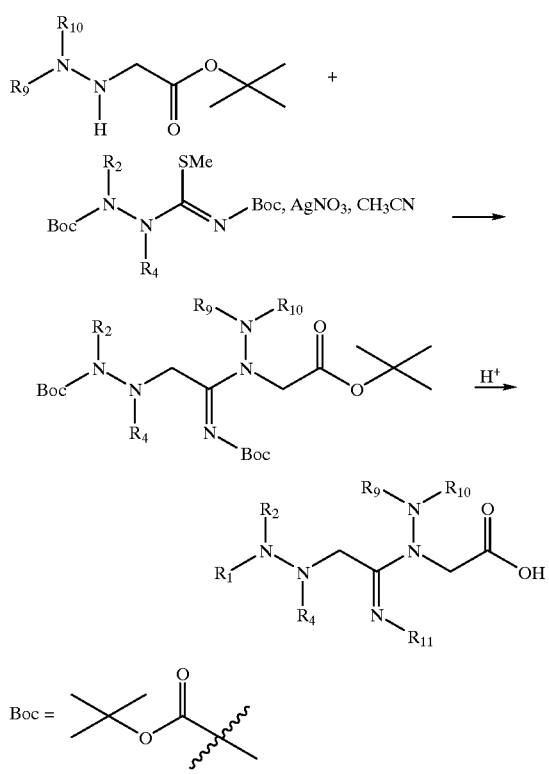

wherein $R_1$–$R_{11}$ are as defined above. For example, preparation of (CAS # 179474-69-2) can be accomplished by the following synthetic procedure:

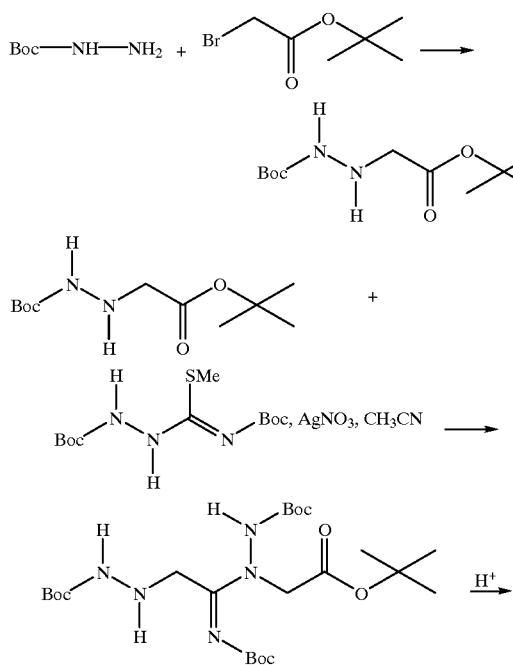

wherein preparation of

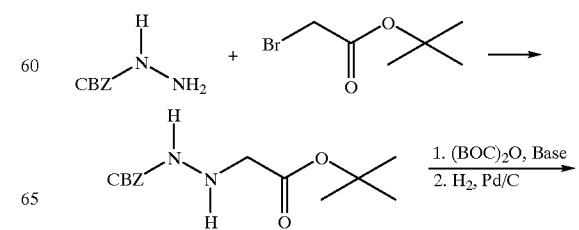

can be accomplished by the following reactions sequence:

[2-(aminoiminomethyl)hydrazino]-acetic acids of the invention can be prepared known synthetic procedures. For example preparation of (CAS # 179474-55-6) can be accomplished by the following synthetic procedure:

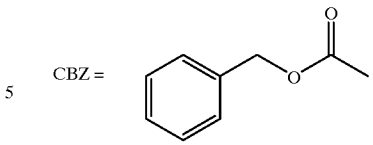

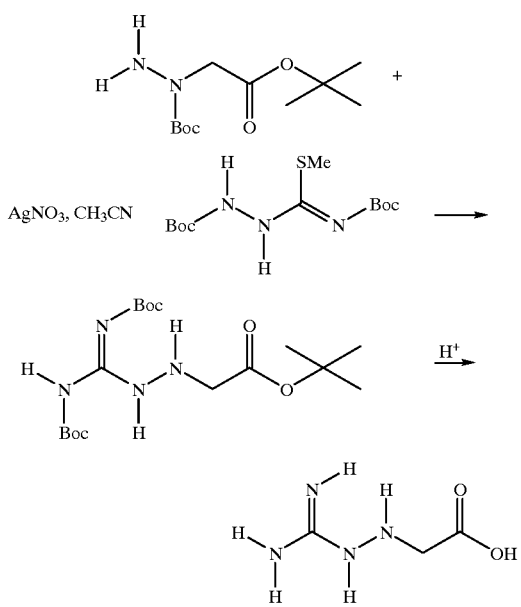

[2-(hydrazinoiminomethyl)hydrazino]-acetic acids of the invention can be prepared known synthetic procedures. For example preparation of (CAS # 179474-62-5) can be accomplished by the following synthetic procedure:

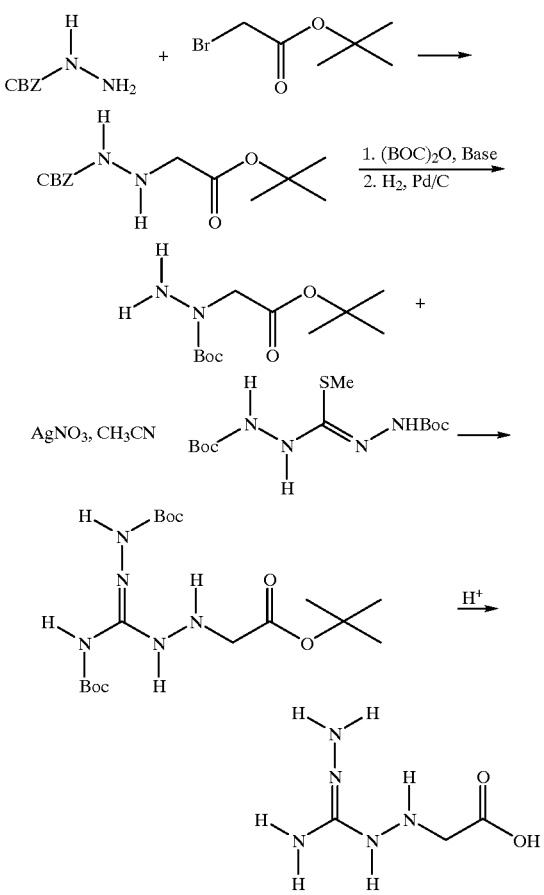

N-(hydrazinoiminomethyl)-glycines of the invention can be prepared known synthetic procedures. For example preparation of (CAS # 17901-84-7) can be accomplished by the following synthetic procedure:

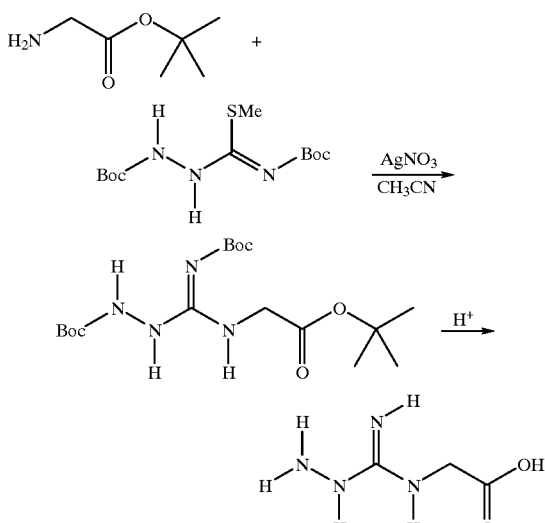

N-(hydrazinohydrazinomethyl)-glycines of the invention can be prepared known synthetic procedures. For example preparation of (CAS # 179474-61-4) can be accomplished by the following synthetic procedure:

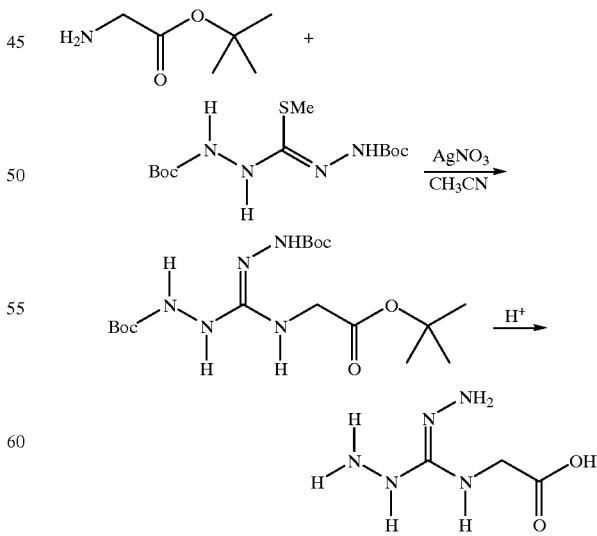

wherein preparation of

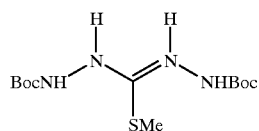

can be accomplished by the following sequence:

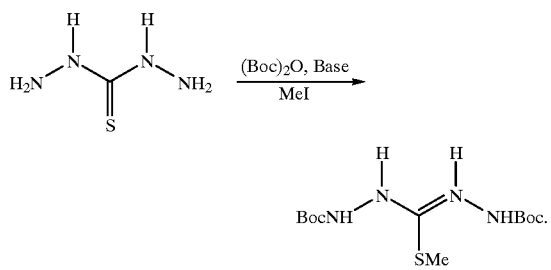

Additionally, analogs of aminoguanidine may be synthesized using conventional techniques (See for example: Larson, Scott D. et al. PCT Int. Appl. WO 96 16,031, the contents of which are hereby expressly incorporated by reference). For example, aminoguanidine can be used as the starting material for synthesizing at least some of the analogs encompassed by formula I. Appropriate synthesis reagents, e.g. alkylating, alkenylating or alkynylating agents may be used to attach the respective groups to target sites. Alternatively, reagents capable of inserting spacer groups may be used to alter the aminoguanidine structure. Sites other than the target site are protected using conventional protecting groups while the desired sites are being targeted by synthetic reagents.

Some specific examples of aminoguanidine compounds of the present invention include cycloaminoguanidine, cycloaminoguanidine phosphate, aminoguanidine, aminoguanidine phosphate (phosphoaminoguanidine), homocycloguanidine and homocycloguanidine phosphate. Cycloaminoguanidine is an essentially planar cyclic analog of aminoguanidine. Although cycloaminoguanidine is structurally similar to aminoguanidine, the two compounds are believed to be distinguishable both kinetically and thermodynamically.

The phosphorylated compound P-cycloaminoguanidine is structurally similar to phosphoaminoguanidine; however, the phosphorous-nitrogen (P-N) bond of cycloaminoguanidine phosphate is believed to be more stable than that of phosphoaminoguanidine. Aminoguanidine compounds which can act as substrates for creatine kinase are at least some of the compounds which are intended to be part of this invention. Examples of such aminoguanidine and diaminoguanidine compounds are included in Table 1.

Salts of the products may be exchanged to other salts using standard protocols. The enzymatic synthesis utilizes the creatine kinase enzyme, which is commercially available, to phosphorylate the aminoguanidine compounds. ATP is required by creatine kinase for phosphorylation, hence it needs to be continuously replenished to drive the reaction forward. It is necessary to couple the creatine kinase reaction to another reaction that generates ATP to drive it forward. The purity of the resulting compounds can be confirmed using known analytical techniques including $^1$H NMR, $^{13}$C NMR Spectra, Thin layer chromatography, HPLC and elemental analysis.

Utility

In the present invention, the aminoguanidine compounds can be administered to an individual (e.g., a mammal), alone or in combination with another compound, for the treatment of diseases of the nervous system. As agents for the treatment of diseases of the nervous system, aminoguanidine compounds can interfere with creatine kinase/phosphocreatine functions, thereby preventing, ameliorating, arresting or eliminating direct and/or indirect effects of disease which contribute to symptoms such as paraplegia or memory impairment. Other compounds which can be administered together with the aminoguanidine compounds include neurotransmitters, neurotransmitter agonists or antagonists, steroids, corti-costeroids (such as prednisone or methyl prednisone) immunomodulating agents (such as betainteferon), immunosuppressive agents (such as cyclophosphamide or azathioprine), nucleotide analogs, endogenous opioids, or other currently clinically used drugs. When co-administered with aminoguanidine compounds, these agents can augment interference with creatine kinase/phosphocreatine cellular functions, thereby preventing, reducing, or eliminating direct and/or indirect effects of disease.

A variety of diseases of the nervous system can be treated with aminoguanidine or aminoguanidine analogs, including but not limited to those diseases of the nervous system described in detail above. Others include bacterial or fungal infections of the nervous system. Aminoguanidine or analogs of aminoguanidine can be used to reduce the severity of a disease, reduce symptoms of primary disease episodes, or prevent or reduce the severity of recurrent active episodes. Aminoguanidine, aminoguanidine phosphate or analogs such as cycloaminoguanidine and cycloaminoguanidine phosphate can be used to treat progressive diseases. Many aminoguanidine analogs can cross the blood-brain barrier. For example, treatment can result in the reduction of tremors in Parkinson's disease, and other clinical symptoms.

Modes of Administration

The aminoguanidine compound can be administered to the afflicted individual alone or in combination with another aminoguanidine analog or other agent. The aminoguanidine compounds can be administered as pharmaceutically acceptable salts in a pharmaceutically acceptable carrier, for example. The compound may be administered to the subject by a variety of routes, including, but not necessarily limited to, oral (dietary), transdermal, or parenteral (e.g., subcutaneous, intramuscular, intravenous injection, bolus or continuous infusion) routes of administration, for example. An effective amount (i.e., one that is sufficient to produce the desired effect in an individual) of a composition comprising a aminoguanidine analog is administered to the individual. The actual amount of drug to be administered will depend on factors such as the size and age of the individual, in addition to the severity of symptoms, other medical conditions and the desired aim of treatment.

The aminoguanidine compound can be formulated according to the selected route of administration (e.g., powder, tablet, capsule, transdermal patch, implantable capsule, solution, emulsion). An appropriate composition comprising a aminoguanidine analog can be prepared in a physiologically acceptable vehicle or carrier. For example, a composition in tablet form can include one or more additives such as a filler (e.g., lactose), a binder (e.g., gelatin, carboxymethylcellulose, gum arabic), a flavoring agent, a coloring agent, or coating material as desired. For solutions or emulsions in general, carriers may include aqueous or alcoholic/aqueous solutions, emulsions or suspensions, including saline and buffered media. Parenteral vehicles can include sodium chloride, solution, Ringer's dextrose, dextrose and sodium chloride, lactated Ringer's or fixed oils.

In addition, intravenous vehicles can include fluid and nutrient replenishers, and electrolyte replenishers, such as those based on Ringer's dextrose. Preservatives and other additives can also be present. For example, antimicrobial, antioxidant, chelating agents, and inert gases can be added. (See, generally, Remington's Pharmaceutical Sciences, 16th Edition, Mack, Ed., 1980).

The term "administration" is intended to include routes of administration which allow the aminoguanidine compounds to perform their intended function(s) of preventing, ameliorating, arresting, and/or eliminating disease(s) of the nervous system in a subject. Examples of routes of administration which may be used include injection (subcutaneous, intravenous, parenterally, intraperitoneally, etc.), oral, inhalation, transdermal, and rectal. Depending on the route of administration, the aminoguanidine-like compound may be coated with or in a material to protect it from the natural conditions which may detrimentally effect its ability to perform its intended function. The administration of the aminoguanidine-like compound is done at dosages and for periods of time effective to reduce, ameliorate or eliminate the symptoms of the nervous system disorder. Dosage regimes may be adjusted for purposes of improving the therapeutic or prophylactic response of the compound. For example, several divided doses may be administered daily or the dose may be proportionally reduced as indicated by the exigencies of the therapeutic situation.

In addition, the methods of the instant invention comprise aminoguanidine compounds effective in crossing the blood-brain barrier.

The aminoguanidine compounds of this invention may be administered alone or as a mixture of aminoguanidine compounds, or together with an adjuvant or other drug. For example, the aminoguanidine compounds may be coadministered with other art recognized moieties such as nucleotides, neurotransmitters, agonists or antagonists, steroids, immunomodulators, immunosuppressants, vitamins, endorphins or other drugs which act upon the nervous system or brain.

Creatine Kinase Isoenzymes in the Brain

Cells require energy to survive and to carry out the multitude of tasks that characterize biological activity. Cellular energy demand and supply are generally balanced and tightly regulated for economy and efficiency of energy use. Creatine kinase plays a key role in the energy metabolism of cells with intermittently high and fluctuating energy requirements such as skeletal and cardiac muscle, brain and neural tissues, including, for example, the retina, spermatozoa and electrocytes. As stated above, the enzyme catalyzes the reversible transfer of the phosphoryl group from creatine phosphate to ADP, to generate ATP. There are multiisoforms of creatine kinase (CK) which include muscle (CK-MM), brain (CK-BB) and mitochondrial (CK-Mia, CK-Mib) isoforms.

Experimental data suggest that CK is located near the sites in cells where energy generation occurs, e.g., where force generation by motor proteins takes place, next to ion pumps and transporters in membranes and where other ATPdependent processes take place. It seems to play a complex multi-faceted role in cellular energy homeostasis.

The creatine kinase system is involved in energy buffering/energy transport activities. It also is involved in regulating ADP and ATP levels intracellularly as well as ADP/ATP ratios. Proton buffering and production of inorganic phosphate are important parts of the system.

In the brain, this creatine kinase system is quite active. Regional variations in CK activity with comparably high levels in cerebellum were reported in studies using native isoenzyme electrophoresis, or enzymatic CK activity measurements in either tissue extracts or cultured brain cells. Chandler et al. Stroke, 19: 251–255 (1988), Maker et al. Exp. Neurol., 38: 295–300 (1973), Manos et al. J. Neurol. Chem., 56: 2101–2107 (1991). In particular, the molecular layer of the cerebellar cortex contains high levels of CK activity (Maker et al. id. (1973) Kahn Histochem., 48: 29–32 (1976) consistent with the recent 3'P-NMR findings which indicate that gray matter shows a higher flux through the CK reaction and higher creatine phosphate concentrations as compared to white matter (Cadoux-Hudson et al. FASEBJ., 3: 2660–2666 (1989), but also high levels of CK activity were 5 shown in cultured oligodendrocytes (Manos et al. id. (1991), Molloy et al. J. Neurochem., 59: 1925–1932 (1992), typical glial cells of the white matter. The brain CK isoenzyme CK-BB is the major isoform found in the brain. Lower amounts of muscle creatine kinase (CK-MM) and mitochondrial creatine kinase (CK-Mi) are found.

Localization and Function of CK Isoenzymes in Different Cells of the Nervous System Brain CK (CK-BB) is found in all layers of the cerebellar cortex as well as in deeper nuclei of the cerebellum. It is most abundant in Bergmann glial cells (BGC) and astroglial cells, but is also found in basket cells and neurons in the deeper nuclei. Hemmer et al., Eur. J. Neuroscience, 6: 538–549 (1994), Hemmer et al. Dev. Neuroscience, 15: 3–5 (1993). The BGC is a specialized type of astroglial cell. It provides the migratory pathway for granule cell migration from the external to the internal granule cell layer during cerebellar development. Another main function of these cells is the proposed ATP-dependent spatial buffering of potassium ions released during the electrical activity of neurons (Newman et al. Trends Neuroscience, 8: 156–159 (1985), Reichenbach, Acad. Sci New York, (1991), pp. 272–286. Hence, CK-BB seems to be providing energy (ATP) for migration as well as K+buffering through regulation of the Na+/K+ ATPase. The presence of CK-BB in astrocytes (Manos et al. id. 1991, Hemmer et al. id. 1994, Hemmer et al. id. 1993) may be related to the energy requirements of these cells for metabolic interactions with neurons; e.g., tricarboxylic acid cycle (TCA) metabolite and neurotransmitter trafficking. Hertz, Can J. Physiol. Pharmacol., 70: 5145–5157 (1991).

The Purkinje neurons of the cerebellum play a very important role in brain function. They receive excitatory input from parallel fibers and climbing fibers, they represent the sole neuronal output structures of the cerebellar cortex. Calcium mediated depolarizations in Purkinje cell dendrites are thought to play a central role in the mechanism of cerebellar motoric learning. Ito Corr. Opin. Neurobiol., 1: 616–620 10 (1991). High levels of muscle CK (CK-MM) were found in Purkinje neurons. Hemmer et al. id. (1994), Hemmer et al., id. (1993). There is strong evidence to support that CK-MM is directly or indirectly coupled to energetic processes needed for Ca++homeostasis or to cellular processes triggered by this second messenger.

The glomerular structures of the cerebellum contain high levels of CK-BB and mitochondrial CK (CK-Mi). Large amounts of energy are needed in these structures for restoration of potassium ion gradients partially broken down during neuronal excitation as well as for metabolic and neurotransmitter trafficking between glial cells and neurons. Hertz et al., id. (1991). The presence of CK in these structures may be an indication that part of the energy consumed in these giant complexes might be supported by the creatine kinase system.

In neurons, CK-BB is found in association with synaptic vesicles (Friedhoff and Lerner, Life Sci., 20: 867–872 (1977) as well as with plasma membranes (Lim et al., J. Neurochem., 41: 1177–1182 (1983)).

There is evidence to suggest that CK is bound to synaptic vesicles and to the plasma membrane in neurons may be involved in neurotransmitter release as well as in the maintenance of membrane potentials and the restoration of ion gradients before and after stimulation. This is consistent with the fact that high energy turnover and concomitantly high CK concentrations have been found in those regions of the brain that are rich in synaptic connections; e.g., in the molecular layer of the cerebellum, in the glomerular structures of the granule layer and also in the hippocampus. The observation that a rise in CK levels observed in a fraction of brain containing nerve endings and synapses, parallels the neonatal increase in Na+/K+ ATPase is also suggestive that higher levels of creatine phosphates and CK are characteristic of regions in which energy expenditure for processes such as ion pumping are large. Erecinska and Silver, *J. Cerebr. Blood Flow and Metabolism*, 9: 2–19 (1989). In addition, protein phosphorylation which plays an important role in brain function is also through to consume a sizable fraction of 40 the total energy available in those cells (Erecinska and Silver, id. 1989). Finally, CK, together with nerve-specific enolase belongs to a group of proteins known as slow component b (SCb). These proteins are synthesized in neuronal cell body and are directed by axonal transport to the axonal extremities. Brady and Lasek, Cell, 23: 515–523 (1981), Oblinger et al., J. Neurol., 7: 433–462 (1987) The question of whether CK participates in the actual energetics of axonal transport remains to be answered.

In conclusion, the CK system plays a key role in the energetics of the adult brain.

This is supported by 31p NMR magnetization transfer measurements showing that the pseudo first order rate constant of the CK reaction in the direction of ATP synthesis as well as CK flux correlate with brain activity which is measured by EEG as well as by the amount of deoxyglucose phosphate formed in the brain after administration of deoxyglucose. The present inventors have discovered that diseases of the nervous system can be treated by modulating the activity of the creatine kinase/creatine phosphate pathway.

The Role of Creatine Kinase in Treating Diseases of the Nervous System

The mechanisms by which nerve cell metabolites are normally directed to specific cell tasks is poorly understood. It is thought that nerve cells, like other cells, regulate the rate of energy production in response to demand. The creatine kinase system is active in many cells of the nervous system and is thought to play a role in the allocation of high energy phosphate to many diverse neurological processes, such as neurotransmitter biosynthesis, electrolyte flux and synaptic communication. Neurological function requires significant energy and creatine kinase appears to play an important role in controlling the flow of energy inside specialized excitable cells such as neurons. The induction of creatine kinase, the BB isozyme and the brain mitochondrial creatine kinase in particular, results in the generation of a high energy state which could sustain or multiply the pathological process in diseases of the nervous system. Creatine kinase induction also causes release of abnormally elevated cellular energy reserves which appear to be associated with certain diseases of the nervous system. Conversely, suppression of the creatine kinase system, or abberances in it, induce a low energy state which could result in or assist in the death in the process of all the nervous system.

The components of the creatine kinase/phosphocreatine system include the enzyme creatine kinase, the substrates creatine and creatine phosphate, and the transporter of creatine. Some of the functions associated with this system include efficient regeneration of energy in cells with fluctuating and high energy demand, phosphoryl transfer activity, ion transport regulation, cytoskeletal association, nucleotide pool preservation, proton buffering, and involvement in signal transduction pathways. The creatine kinase/phosphocreatine system has been shown to be active in neurons, astrocytes, oligodendrocytes, and Schwann cells. The activity of the enzyme has been shown to be up-regulated during regeneration and down-regulated in degenerative states, and aberrant in mitochondrial diseases.

Many diseases of the nervous system are thought to be associated with abnormalities in an energy state which could result in imbalanced ion transport neurotransmitter release and result in cell death. It has been reported that defects in mitochondrial respiration enzymes and glycolytic enzymes may cause impairment of cell function.

Without wishing to be bound by theory, it is thought that if the induction or inhibition of creatine kinase is a cause or a consequence of disease, modulating its activity, may block the disease. Modulating its activity would modulate energy flow and affect cell function. Alternatively, another possibility is that creatine kinase activity generates a product which affects neurological function. For example, creatine phosphate may donate a phosphate to a protein to modify its function (e.g., activity, location). If phosphocreatine is such a phosphate donor, aminoguanidine analogs which are phosphorylatable or phosphoaminoguanidine analogs may competitively inhibit the interaction of phosphocreatine with a target protein thereby directly or indirectly interfering with nervous system functions. Alternatively, phosphorylatable aminoguanidine analogs with altered phosphoryl group transfer potential may tie up phosphate stores preventing efficient transfer of phosphate to targets. A neurological disease could be associated with down regulation of creatine kinase activity. In such cases, replenishment of the substrates, e.g., aminoguanidine, aminoguanidine phosphate or a substrate analog, which could sustain ATP production for an extended of time, with other activators of the enzyme could be beneficial for treatment of the disease.

Ingestion of creatine analogs has been shown to result in replacement of tissue phosphocreatine pools by synthetic phosphagens with different kinetic and thermodynamic properties. This results in subtle changes of intracellular energy metabolism, including the increase of total reserves of high energy phosphate (see refs. Roberts, J. J. and J. B. Walker, *Arch Biochem. Biophys* 220(2): 563–571 (1983)). The replacement of phosphocreatine pools with slower acting synthetic phosphagens, such as creatine analogs might benefit neurological disorders by providing a longer lasting source of energy. One such analog, cyclocreatine (1-carboxymethyl-2-aminoimidazolidine) modifies the flow of energy of cells in stress and may interfere with ATP utilization at sites of cellular work.

The pathogenesis of nerve cell death in neurodegenerative diseases is unknown. A significant amount of data has supported the hypothesis that an impairment of energy metabolism may underlie the slow exitotoxic neuronal death. Several studies have demonstrated mitochondrial or oxidative defects in neurodegenerative diseases. Impaired energy metabolism results in decreases in high energy phosphate stores and a deteriorating membrane potential. Under these conditions the voltage sensitive Mg2+block of NMDA receptors is relieved, allowing the receptors to be persistently activated by endogenous concentrations of glutamate. In this way, energy related metabolic defects may lead to neuronal death by a slow exitotoxic mechanism. Recent studies indicate that such a mechanism occurs in vivo, and it may play a role in animal models of Huntington's disease and Parkinson's disease.

As discussed in detail above, the creatine kinase/creatine phosphate energy system is only one component of an elaborate energy-generating system found in the nervous system. The reaction catalyzed by this system results in the rapid regeneration of energy in the form of ATP at sites of cellular work. In the mitochondria the enzyme is linked to the oxidative phosphorylation pathway that has been implicated in diseases of the nervous system. There the enzyme works in the reverse direction where it stores energy in the form of creatine phosphate.

The contents of all references, pending patent applications and published patent applications, cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating or preventing a disease of the nervous system in a subject in need thereof comprising administering to said subject a therapeutically effective amount of an aminoguanidine, wherein said aminoguanidine has the formula:

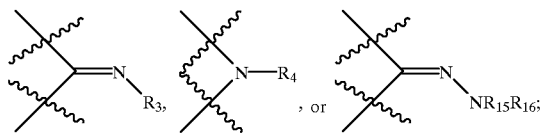

wherein a) $R_1$ through $R_{16}$, if present, are selected from the group consisting of hydrogen, alkyl, alkenyl, alkynyl, and alkoxyl;

b) J is either

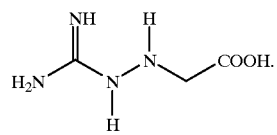

c) Q is either

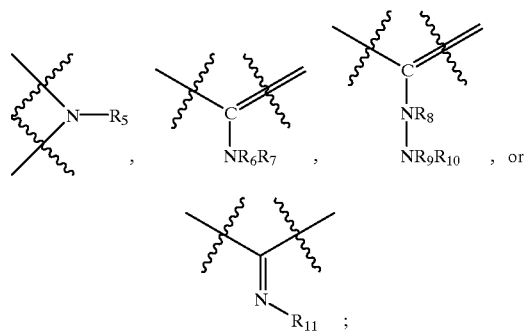

d) T, if present, is $R_{12}$ or $NR_{13}R_{14}$;

e) Y is an alkylene, alkenylene, alkynylene or an alkoxylene;

f) Z is selected from the group consisting of

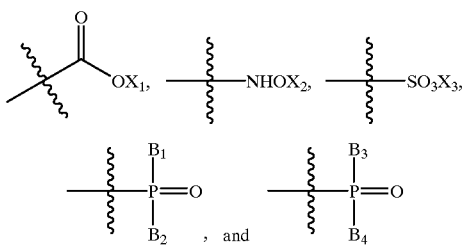

wherein $B_1-B_4$ are each independently selected from hydrogen and $OX_4$ and $X_1-X_4$ are each independently selected from the group consisting of hydrogen, alkyl, alkenyl, alkynyl and pharmaceutically acceptable salts; and wherein Y and Q or N and Q can form a ring structure.

2. The method of claim 1, wherein said treating comprises reducing or eliminating symptoms associated with a preexisting disease of the nervous system.

3. The method of claim 1, wherein said preventing comprises preventing the occurrence of diseases of the nervous system within said subject.

4. The method of claim 1, wherein said aminoguanidine compound is

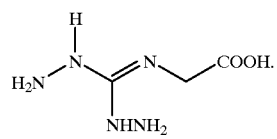

5. The method of claim 1, wherein said aminoguanidine compound is

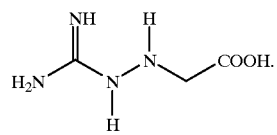

6. The method of claim 1, wherein said aminoguanidine compound is

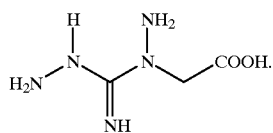

7. The method of claim 1, wherein said aminoguanidine compound is

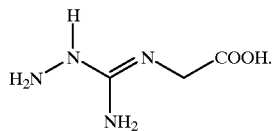

8. The method of claim 1, wherein said aminoguanidine compound is

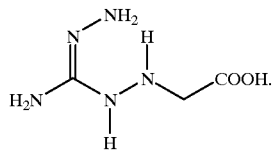

9. The method of claim 1, wherein said disease of the nervous system is selected, from the group consisting of neuropathies, Alzheimer's disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, dementia, peripheral nervous system diseases and mental disorders.

10. The method of claim 9, wherein said aminoguanidine is selected from the group consisting of

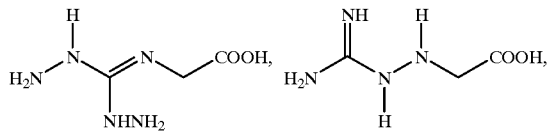

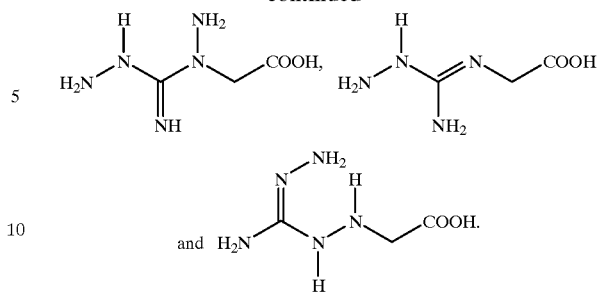

11. The method of claim 1, further comprising coadministering to said subject a neurotransmitter, a neurotransmitter analog, a steroid, an immunomodulating agent, or an immune suppressive agent.

12. The method of claim 1, wherein said subject is treated for diseases of the nervous system by reducing or eliminating symptoms associated with a preexisting disease of the nervous system.

13. A method of alleviating toxic side effects of a drug used to treat a nervous system disease in a subject in need thereof, comprising administering to said subject a therapeutically effective amount of an aminoguanidine or a pharmaceutically acceptable salt thereof, sufficient to prevent, reduce, ameliorate, or alleviate toxic side effects of said drug used to treat the nervous system disease in said subject, wherein said aminoguanidine is selected from the group consisting of

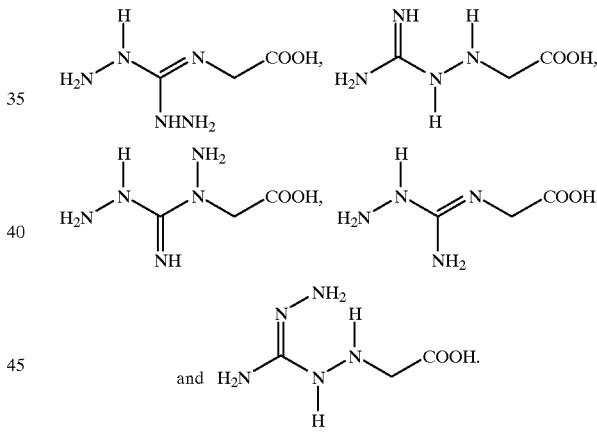

* * * * *